(12) United States Patent
Hughes et al.

(10) Patent No.: US 7,931,909 B2
(45) Date of Patent: Apr. 26, 2011

(54) OCULAR THERAPY USING ALPHA-2 ADRENERGIC RECEPTOR COMPOUNDS HAVING ENHANCED ANTERIOR CLEARANCE RATES

(75) Inventors: Patrick M. Hughes, Aliso Viejo, CA (US); James A. Burke, Santa Ana, CA (US); Joan-En Chang-Lin, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 563 days.

(21) Appl. No.: 11/416,929

(22) Filed: May 2, 2006

(65) Prior Publication Data

US 2006/0257452 A1 Nov. 16, 2006

Related U.S. Application Data

(60) Provisional application No. 60/679,771, filed on May 10, 2005.

(51) Int. Cl.
*A61K 9/00* (2006.01)
(52) U.S. Cl. .................................. 424/400; 424/427
(58) Field of Classification Search .................. None
See application file for complete search history.

(56) References Cited

U.S. PATENT DOCUMENTS

| | | | | |
|---|---|---|---|---|
| 4,327,725 A | 5/1982 | Cortese et al. | ............... | 128/260 |
| 4,474,451 A | 10/1984 | Mizokami | ............... | 354/418 |
| 4,521,210 A | 6/1985 | Wong | ............... | 604/8 |
| 4,853,224 A | 8/1989 | Wong | ............... | 424/427 |
| 4,997,652 A | 3/1991 | Wong | ............... | 424/428 |
| 5,164,188 A | 11/1992 | Wong | ............... | 424/428 |
| 5,443,505 A | 8/1995 | Wong et al. | ............... | 623/4 |
| 5,501,856 A | 3/1996 | Ohtori et al. | ............... | 424/428 |
| 5,766,242 A | 6/1998 | Wong et al. | ............... | 623/4 |
| 5,824,072 A | 10/1998 | Wong | ............... | 623/4 |
| 5,869,079 A | 2/1999 | Wong et al. | ............... | 424/426 |
| 6,074,661 A | 6/2000 | Olejnik et al. | ............... | 424/427 |
| 6,242,442 B1 * | 6/2001 | Dean et al. | ............... | 514/222.8 |
| 6,331,313 B1 | 12/2001 | Wong et al. | ............... | 424/427 |
| 6,369,116 B1 | 4/2002 | Wong et al. | ............... | 514/913 |
| 6,699,493 B2 | 3/2004 | Wong | ............... | 424/428 |
| 2003/0060763 A1 | 3/2003 | Penfold et al. | ............... | 604/116 |

FOREIGN PATENT DOCUMENTS

| | | |
|---|---|---|
| WO | WO 03/077952 | 9/2003 |
| WO | WO 2005/107705 | 11/2005 |
| WO | WO 2005/110362 | 11/2005 |
| WO | WO 2005/110367 | 11/2005 |
| WO | WO 2005/110368 | 11/2005 |

OTHER PUBLICATIONS

Merkli, A., et al., *Use of Insoluble Biodegradable Polymers in Ophthalmic Systems for the Sustained Release of Drugs*, European Journal of Pharmaceutics and Biopharmaceutics, Elsevier Science Publishers B.V., 1995, vol. 31, No. 5, pp. 271-283.

Barza et al., "The effects of infection and probenecid on the transport of carbenicillin from the rabbit vitreous humor", Invest Ophthalmol Vis. Sci., 22:720-726 (1982).
Cheng et al., "Treatment or prevention of herpes simplex virus retinitis with intravitreally injectable crystalline 1-O-Hexadecylpropanediol-3-phospho-ganciclovir", (2002) Investigative Ophthalmology & Visual Science, 43(2):515-521.
Cunha-Vaz et al., "The active transport of fluoroscein by the retinal vessels and the retina", J. Physiol., 191:467-486 (1967).
Cunha-Vaz, "The blood-ocular barriers", Surv. Ophthalmol., 5:279-296 (1979).
Han et al., "Characterization of a Novel Cationic Drug Transporter in Human Retinal Pigment Epithelial Cells", Journal of Pharmacology and Experimental Therapeutics, 296(2): 450-457, 2001.
Heller, Biodegradable Polymers in Controlled Drug Delivery, In: CRC Critical Reviews in Therapeutic Drug Carrier Systems, vol. 1, CRC Press, Boca Raton, FL 1987, pp. 39-90.
Lesar et al., "Antimicrobial drug delivery to the eye", Drug Intell Clin. Pharm., 19:642-654 (1985).
Maurice et al., "Handbook of Experimental Pharmacology: Pharmacology of the Eye", Sears, Eds., vol. 69, (Springer-Verlag, Berlin-Heidelberg), 19-116 (1986).
Maurice, "Protein dynamics in the eye studied with labelled proteins", Am J Ophthalmol, 49:361-367 (1959).
Maurice, "The exchange of sodium between the vitreous body and the blood and aqueous humor", J. Physiol, 137:110-125 (1957).
Miller et al., "Fleroxacin pharmacokinetics in aqueous and vitreous humors determination by using complete concentration-time data from individual rabbits", Antimicrob. Agents. Chemother., 36:32-38 (1992).
Sugiura et al., "Effects of intraocular pressure change on movement of FITC-dextran across vitreous-aqueous interface", (1989), Jpn J. Ophthalmol, 33(4):441-450.
USP 23; NF 18 (1995) pp. 1790-1798.

* cited by examiner

*Primary Examiner* — Michael G Hartley
*Assistant Examiner* — Nissa M Westerberg
(74) *Attorney, Agent, or Firm* — Joel B. German; Debra D. Condino; Allergan, Inc.

(57) ABSTRACT

Ophthalmically therapeutic materials, such as liquid-containing compositions and polymeric drug delivery systems, include a therapeutic component which includes an alpha 2 adrenergic receptor agonist that is cleared from the anterior segment of an individual's eye to which the material is administered. The alpha 2 adrenergic receptor agonist may have a vitreal half-life greater than about three hours. The present materials are effective in treating an ocular condition(s) that affect the anterior segment of an eye, or the anterior and posterior segment of the eye. The materials are suitable for intravitreal or periocular administration and can provide prolonged drug delivery and therapeutic benefits to patients to which the materials have been administered. The alpha 2 adrenergic receptor agonists can be provided in liquid-containing formulations and/or bioerodible and/or non-bioerodible polymeric implants and microparticles. Methods of making and using the present materials are also described.

9 Claims, 1 Drawing Sheet

OCULAR THERAPY USING ALPHA-2 ADRENERGIC RECEPTOR COMPOUNDS HAVING ENHANCED ANTERIOR CLEARANCE RATES

CROSS-REFERENCE TO RELATED APPLICATIONS

The present application claims the benefit of U.S. Application No. 60/679,771, filed May 10, 2004, the content of which in its entirety is hereby incorporated by reference.

BACKGROUND

The present invention generally relates to the use of alpha-2 adrenergic receptor agents that are cleared from the anterior of an eye to treat an eye of a patient, and more specifically to ophthalmic compositions and drug delivery systems that provide extended release of the alpha-2 adrenergic receptor agents to an eye to which the agents are administered; and to methods of making and using such compositions and systems, for example, to treat or reduce one or more symptoms of an ocular condition to improve or maintain vision of a patient.

In ocular therapies, alpha agonists (e.g., agonists of alpha adrenergic receptors) are used to reduce aqueous humor production and increase aqueous humor outflow through the trabecular meshwork. The outflow through the trabecular meshwork accounts for about 90% of the eye's fluid drainage capability, and the remaining approximately 10% is provided by the uveoscleral outflow where fluid flows into the ciliar muscle beneath the trabecular meshwork. Two examples of alpha agonists used for ocular therapy include apraclonidine (IOPIDINE) and brimonidine-P (ALPHAGAN-P).

Brimonidine, 5-bromo-6-(2-imidazolidinylideneamino) quinoxaline, is an alpha-2-selective adrenergic receptor agonist that is effective in the treatment of open-angle glaucoma by decreasing aqueous humor production and increasing uveoscleral outflow. Apraclonidine generally has, a mixed alpha-1 and alpha-2 stimulatory activity. Brimonidine is available in two chemical forms, brimonidine tartrate and brimonidine free base. Brimonidine tartrate (Alphagan® P) is publicly available by Allergan for treating glaucoma. Topical ocular brimonidine formulation, 0.15% Alphagan® P (Allergan, Irvine, Calif.), is currently commercially available for treatment of open-angle glaucoma. The solubility of brimonidine tartrate in water is, 34 mg/mL in water and 2.4 mg/mL in a pH 7.0 phosphate buffer while the solubility of brimonidine freebase is negligible in water.

Recent studies have suggested that brimonidine can promote survival of injured retinal ganglion nerve cells by activation of the alpha-2-adrenoceptor in the retina and/or optic nerve. For example, brimonidine can protect injured neurons from further damage in several models of ischemia and glaucoma.

Glaucoma-induced ganglion cell degeneration is one of the leading causes of blindness. This indicates that brimonidine can be utilized in a new therapeutic approach to glaucoma management in which neuroprotection and intraocular pressure reduction are valued outcomes of the therapeutic regimen. For brimonidine to protect the optic nerve, however, it must have access to the posterior segment of the eye at therapeutic levels. Currently available techniques for administering brimonidine to the posterior chamber of the eye are not sufficient to address this issue.

Agents that are administered to the vitreous of an eye of a patient can be eliminated from the vitreous by diffusion to the retro-zonular space (anterior clearance) with clearance via the aqueous humor, such as through the trabecular meshwork outflow and the uveoscleral outflow, or by trans-retinal elimination (posterior clearance). Most compounds that are relatively hydrophilic to moderately lipophilic utilize the former (anterior clearance) pathway unless a facilitated or active transport mechanism exists for these while extremely lipophilic compounds and those with trans-retinal transport mechanisms will utilize the latter (i.e., will go out through the retina). For example, macromolecules and peptides, including antibiotics, are often eliminated via the anterior route. In comparison, existing alpha 2 adrenergic receptor agonists are eliminated via the posterior route. This is most likely the result of an organic cationic transport mechanism in the outer blood retinal barrier, the RPE. Unfortunately, compounds that are eliminated across the retina have extremely short intravitreal half-lives. Additionally, these compounds tend to have extremely small aqueous humor/vitreous humor concentration ratios at steady-state. This dramatically impacts the treatment of anterior tissues from posterior administration of such compounds.

Intravitreal delivery of therapeutic agents can be achieved by injecting a liquid-containing composition into the vitreous, or by placing polymeric drug delivery systems, such as implants and microparticles, into the vitreous. Examples of biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493.

Other ocular therapies may include periocular delivery of drugs to a patient. Penetration of drugs directly into the posterior segment of the eye is restricted by the blood-retinal barriers. The blood-retinal barrier is anatomically separated into inner and outer blood barriers. Movement of solutes or drugs into the internal ocular structures from the periocular space is restricted by the retinal pigment epithelium (RPE), the outer blood-retinal barrier. The cells of this structure are joined by zonulae oclludentae intercellular junctions. The RPE is a tight ion transporting barrier that restricts paracellular transport of solutes across the RPE. The permeability of most compounds across the blood-retinal barriers is very low. Extremely lipophilic compounds, however, such as chloramphenical and benzyl penicillin, can penetrate the blood-retinal barrier achieving appreciable concentrations in the vitreous humor after systemic administration. The lipophilicity of the compound correlates with its rate of penetration and is consistent with passive cellular diffusion. The blood retinal barrier, however, is impermeable to polar or charged compounds in the absence of a transport mechanism. Hydrophilic to moderately lipophilic drugs can diffuse into the iris-ciliary body achieving very low posterior chamber or iris root concentrations. Anterior bulk flow of aqueous humor competes with the posterior elimination of drugs. For compounds that cannot passively penetrate the RPE, but are eliminated across the retina, it is extraordinarily difficult to achieve therapeutic concentrations of drugs at reasonable doses due to the differential rate processes involved.

Thus, there remains a need for new agents that can be used to treat ocular conditions, and that have different pharmacokinetic properties than existing agents.

SUMMARY

Ophthalmically therapeutic materials, such as liquid-containing compositions and polymeric drug delivery systems, include a therapeutic component which includes an alpha 2 adrenergic receptor agonist that is cleared from the anterior segment of an individual's eye to which the material is administered. The alpha 2 adrenergic receptor agonist may have a vitreal half-life greater than about three hours. The present materials are effective in treating an ocular condition(s) that affect the anterior segment of an eye, or the anterior and posterior segment of the eye. The materials are suitable for intravitreal or periocular administration and can provide prolonged drug delivery and therapeutic benefits to patients to which the materials have been administered. The alpha 2 adrenergic receptor agonists can be provided in liquid-containing formulations and/or bioerodible and/or non-bioerodible polymeric implants and microparticles. Methods of making and using the present materials are also described.

Ophthalmically therapeutic materials in accordance with the disclosure herein comprise a therapeutic component that comprises a therapeutically effective amount of an alpha 2 adrenergic receptor agonist having a structure effective in providing elimination of the agonist from the anterior chamber of an eye to which the agonist is administered.

The anteriorly cleared alpha-2 adrenergic receptor agonists of the present materials may be an agonist or agent that selectively activates alpha-2 adrenergic receptors, for example by binding to an alpha-2 adrenergic receptor, relative to other types of adrenergic receptors, such as alpha-1 adrenergic receptors. The selective activation can be achieved under different conditions, but preferably, the selective activation is determined under physiological conditions, such as conditions associated with an eye of a human or animal patient.

A method of producing the present ophthalmically therapeutic materials may comprise selecting an alpha 2 adrenergic receptor agonist that has a vitreous half-life greater than about 3 hours; and combining the selected alpha 2 adrenergic receptor agonist with a liquid carrier component or a polymeric component to form a material suitable for administration to an eye.

Methods of treating one or more ocular conditions comprise a step of administering the present materials to an eye of a patient. The materials can be intravitreally administered and/or periocularly administered. When drug delivery systems are used to deliver the anteriorly cleared alpha 2 adrenergic receptor agonists, sustained delivery and prolonged therapeutic benefits can be obtained.

Kits in accordance with the present invention may comprise one or more of the present materials, and instructions for using the materials. For example, the instructions may explain how to administer the materials to a patient, and types of conditions that may be treated with the materials.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description, examples, and claims, particularly when considered in conjunction with the accompanying drawings.

DESCRIPTION

Figure 1:
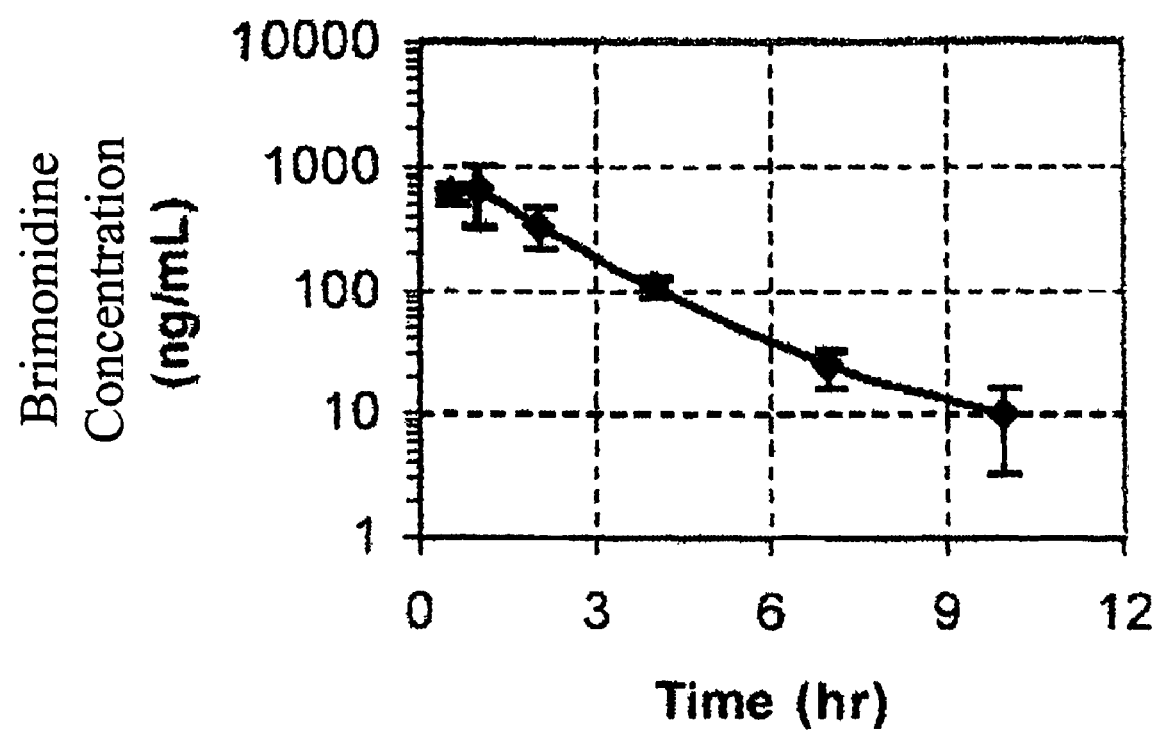
FIG. 1 is a graph of the vitreal concentration of brimonidine as a function of time after a single intravitreal administration of 928 ng of brimonidine into the vitreous of rabbit eyes (n=4).

Ophthalmically therapeutic materials and methods have been invented which provide effective treatment of ocular conditions, such as disorders or diseases of the anterior and/or posterior segment of an eye of an individual, such as a human or animal. The present ophthalmically therapeutic materials comprise a therapeutic component which comprises an alpha 2 adrenergic receptor agonist. The alpha 2 adrenergic receptor agonists of the present materials have structures that are effective in providing anterior clearance or elimination of the agonist from the eye. For example, the alpha 2 adrenergic receptor agonists of the present materials have structures that are effective in permitting the agonists to be cleared via the anterior route or the anterior chamber, as compared to the posterior route or via the retina of an eye to which the materials are administered. Thus, the present materials can provide one or more therapeutic effects for treating anterior ocular conditions, posterior ocular conditions, and combinations of anterior and posterior ocular conditions. For example, the present materials can reduce elevated intraocular pressure in an eye, can provide neuroprotection, and treat glaucoma, and/or can reduce intraocular pressure and provide neuroprotection.

DEFINITIONS

For the purposes of this description, we use the following terms as defined in this section, unless the context of the word indicates a different meaning.

As used herein, an "intraocular drug delivery system" refers to a device or element that is structured, sized, or otherwise configured to be placed in an eye. The present drug delivery systems are generally biocompatible with physiological conditions of an eye and do not cause unacceptable or undesirable adverse side effects. The present drug delivery systems may be placed in an eye without disrupting vision of the eye. The present drug delivery systems may be in the form of a plurality of particles, such as microparticles, or may be in the form of implants, which are larger in size than the present particles. Intraocular drug delivery systems described herein include a polymeric component.

As used herein, a "composition" refers to a material suitable for administration to an eye of an individual. Compositions may include a polymeric drug delivery systems if desired. Compositions may comprise a liquid carrier, and compositions refers to material such as solutions, suspensions, emulsions, and the like.

As used herein, a "therapeutic component" refers to a portion of a drug delivery system or composition comprising one or more therapeutic agents, active ingredients, or substances used to treat a medical condition of the eye. The therapeutic component may be a discrete region of an intraocular implant, or it may be homogenously distributed throughout the implant or particles or composition. The therapeutic agents of the therapeutic component are typically ophthalmically acceptable, and are provided in a form that does not cause adverse reactions when the ophthalmically therapeutic material is placed in an eye.

As used herein, "associated with" means mixed with, dispersed within, coupled to, covalently bonded, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the iris but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute-macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time occurs concurrent with or subsequent to release of the therapeutic agent. The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

The present materials described herein include, without limitation, liquid-containing compositions, such as formulations, and polymeric drug delivery systems. The present compositions may be understood to include solutions, suspensions, emulsions, and the like, such as other liquid-containing compositions used in ophthalmic therapies. Polymeric drug delivery systems comprise a polymeric component, and may be understood to include biodegradable implants, nonbiodegradable implants, biodegradable microparticles, such as biodegradable microspheres, and the like. The present drug delivery systems may also be understood to encompass elements in the form of tablets, wafers, rods, sheets, and the like. The polymeric drug delivery systems may be solid, semisolid, or viscoelastic.

The agonists of the present materials refer to agents that bind or interact with a target receptor, such as a receptor expressed on a cell surface, and activate that target receptor. As used herein, the alpha 2 adrenergic receptor agonist is an agent that selectively interacts with alpha 2 adrenergic receptors. For example, an alpha 2 adrenergic receptor agonist of the present material is typically an agent that selectively activates alpha-2 adrenergic receptors relative to alpha-1 adrenergic receptors. In certain materials, the alpha-2 adrenergic receptor agonist selectively activates or stimulates a subtype of the alpha-2 adrenergic receptors. For example, the agonist may selectively activate one or more of the alpha-2a, the alpha-2b, or the alpha-2c receptors, under certain conditions, such as physiological conditions. The present agonists may partially activate or fully activate alpha 2 adrenergic receptors. The present agonists may also be understood to encompass modified or engineered alpha 2 adrenergic receptor agonists, such as a conventional or publicly known alpha 2 adrenergic receptor agonist that has been modified or engineered to have the desired anterior clearance described herein. Modified or engineered alpha 2 adrenergic receptor agonists interact with alpha 2 adrenergic receptors to activate the receptors, but differ from other alpha 2 adrenergic receptor agonists at least by the clearance of such agonists from the eye. For purposes of convenience, the alpha 2 adrenergic receptor agonists of the present materials may also be referred to as "anteriorly cleared alpha 2 adrenergic receptor agonists".

Certain embodiments of the present materials comprise a therapeutic component that comprises an alpha 2 adrenergic receptor-agonist that is preferentially cleared via the anterior segment of an eye relative to the posterior segment of the eye. Or, stated differently, the alpha 2 adrenergic receptor agonist is cleared from the eye by mixing with the aqueous humor present in the anterior and/or posterior chambers of an eye or through the iris-cilary body, as opposed to being cleared via the retina of the eye. In certain embodiments, the alpha 2 adrenergic receptor agonist has an anterior clearance rate that is at least 30% greater than a posterior clearance rate. For example, the alpha 2 adrenergic receptor agonist may have an anterior clearance rate that is at least about 40% greater, or 50% greater, or 60% greater, or 70% greater, or 90% greater than the posterior clearance rate. Thus the alpha 2 adrenergic receptor agonists have a greater anterior clearance rate/posterior clearance rate ratio than other alpha 2 adrenergic receptor agonists that are cleared via the retina. In addition, the alpha 2 adrenergic receptor agonists may have a high aqueous humor/vitreous humor concentration ratio. The enhanced anterior clearance can be observed when the alpha 2 adrenergic receptor agonist is administered intraocularly, such as into the posterior segment of an eye, such as into the vitreous of an eye, and can be observed when the alpha 2 adrenergic receptor agonist is administered periocularly, such as when the agent is administered into one or more of the following regions: retrobulbar regions, subconjunctival regions, sub-tenon regions, suprachoroidal regions, and intrascleral regions. In many situations, the alpha 2 adrenergic receptor agonist will be cleared from the eye by passing from the anterior chamber through the trabecular meshwork at the angle or the filtration angle.

In other embodiments, the alpha 2 adrenergic receptor agonist has a substantially equal anterior and posterior clearance rate. Importantly, the present materials comprise an alpha 2 adrenergic receptor agonist that has a measurable anterior clearance. For example, when administered to the vitreous of an eye, a sample of the aqueous humor obtained from an individual will contain a measurable amount of the alpha 2 adrenergic receptor agonist after a certain time period. In comparison, existing alpha 2 adrenergic receptor agonists, such as brimonidine, are not detected or are not calculable in the aqueous humor when administered intravitreally or periocularly, as discussed herein.

As discussed above, the therapeutic component of the present materials may comprise a modified or engineered alpha-2 adrenergic agonist. For example, the modified or engineered alpha-2 adrenergic agonist may comprise a base structure effective in interacting with or activating an alpha-2 adrenergic receptor, and a bulking agent or modifier component associated with the base structure to provide an enhanced anterior clearance relative to an identical base structure without the bulking agent or modifier component. The bulking agent or modifier component may be coupled to or covalently bonded with the base structure. For example, the bulking agent or modifier component may be directly covalently bonded to the base structure, or it may be indirectly coupled to the base structure via one or more linking agents. The bulking agent or modifier component can alter the hydrophilicity or lipophilicity of the base structure to achieve the desired anterior clearance. Preferably, the bulking agent or modifier component does not substantially interfere with the base structure's interaction with an alpha-2 adrenergic receptor.

Some modified or engineered alpha-2 adrenergic receptor agonists may comprise a bulking agent or modifier component associated with the base structure in a manner which permits the bulking agent or modifier component to disassociate from the base structure under certain conditions. For example, a bulking agent may be temporarily bonded with the base structure, and after a certain amount of time, the bond degrades and the base structure is released from the bulking agent. The bond may be sensitive to light passing through the eye, or it may be sensitive to one or more chemical agents that can be topically applied to the eye. Or, the base structure may be complexed with the bulking agent or modifier component, and the complex dissociates, over time in the vitreous of an eye.

One non-limiting example of a modified or engineered alpha-2 adrenergic receptor agonist that has a relatively long vitreal half-life is an alpha-2 adrenergic receptor agonist coupled to a polyethylene glycol (PEG). For example, a PEG agent may be covalently bonded to an amino or sulfhydryl group present on the alpha-2 adrenergic receptor agonist via a chemically reactive group on the PEG agent. The resulting modified or engineered alpha-2 adrenergic receptor agonist can be linear or branched in structure. In certain embodiments, the PEG agent has a molecular weight from about 30 kDa to about 60 kDa, for example about 40 kDa or about 50 kDa.

A second non-limiting example of a modified or engineered alpha-2 adrenergic receptor agonist that has a relatively long vitreal half-life is an alpha-2 adrenergic receptor agonist that includes one or more lipophilic components. For example, the alpha-2 adrenergic receptor agonist may be coupled to a hydrophobic hydrocarbon including one or more hydrophilic groups. One example of such an agent includes hydroxy-containing hydrocarbons. Such agents can be effective to provide both hydrophobic and hydrophilic groups and thereby alter the vitreal-half life of the alpha-2 adrenergic agonist. One specific example of a modified or engineered alpha-2 adrenergic receptor agonist includes alkylpropanediol coupled to an alpha-2 adrenergic receptor agonist. Additional examples include alkylpropanediols other than 1-O-hexadecylpropanediol. 1-O-hexadecylpropanediol has been shown to be effective in slowing the release of ganciclovir into the vitreous of rabbit eyes (Cheng et al., "Treatment or prevention of herpes simplex virus retinitis with intravitreally injectable crystalline 1-O-Hexadecylpropanediol-3-phospho-ganciclovir", (2002) Investigative Ophthalmology & Visual Science, 43(2):515-521).

Additional examples of suitable bulking agents or modifier components can be identified and obtained using routine methods known to persons of ordinary skill in the art. Thus, the alpha 2 adrenergic receptor agonists of the present therapeutic components can be identified by screening the agents for the desired pharmacokinetic properties, such as vitreal half-life, aqueous humor/vitreous humor concentration ratios, and the like, using the methods described above. The screened or selected alpha 2 adrenergic receptor agonists can then be combined with one or more components or component precursors of the present compositions and drug delivery systems.

The bulking agent or modifier component may be effective in increasing the molecular weight of the alpha 2 adrenergic receptor agonists. With the increased molecular weight, the alpha 2 adrenergic receptor agonists may exhibit a reduced posterior clearance rate from an eye, and/or may exhibit an enhanced anterior clearance from the eye. One example of a modified alpha 2 adrenergic receptor agonist includes a brimonidine base structure coupled or associated with a polyethylene glycol. The alpha-2 adrenergic agonist of the therapeutic component may have a greater aqueous humor/vitreous humor concentration ratio and greater vitreal half-life relative to other alpha-2 adrenergic receptor agonists, such as brimonidine.

Another example of a modified or engineered alpha-2 adrenergic receptor agonist that has a relatively long vitreal half-life is an alpha-2 adrenergic receptor agonist that prevents trans RPE transport by the organic cation transporters. At physiologic pH many of the alpha 2 adrenergic receptor agonists are positively charged. Transport of organic cations can be mediated by substrate-specific, sodium-dependent transporters and by less specific sodium-independent transporters. Two major families of organic cation transporters have been identified: organic cation transporters (OCT) and organic cation/carnitine transporters (OCTN). The OCT transporters have been identified in the retinal pigmented epithelium (the outer blood-retinal barrier). Additionally, a novel organic cation transporter, distinct from the known OCT family, has been identified in the RPE.

Brimonidine is a substrate for the organic cation transporter present in the conjunctiva. It is possible that elimination of brimonidine across the retina/RPE may be a result of an organic cation transporter. The pKa of the imidazole nitrogen on brimonidine is 7.78.

Thus, the present alpha 2 adrenergic receptor agonists may be effective agents in activating alpha 2 adrenergic receptors without being a substrate for organic cation transporters. Such agonists may not necessarily include a bulking agent, as described above. For example, generating an N-Mannich base prodrug may create a compound that is not a substrate for the organic cation transporters. Another example of the present alpha-2 adrenergic receptor agonists that could possess a decreased organic cation transport is a sulfonyl prodrug of brimonidine. These compounds would be expected to have a decreased transretinal elimination and prolonged vitreous half-life. Synthesis of these compounds is straight forward by those skilled in the art.

Thus, certain embodiments of the present alpha 2 adrenergic receptor agonists may be non-cationic at a physiological pH, such as at the pH of the interior of an eye. In other words, the present agonists can be present as neutrally charged or anionic molecules in the interior of an eye. In certain embodiments, the present agonists are non-cationic at a pH from about 6.0 to about 7.8. For example, the present agonists are non-cationic at a pH from about 7.0 to about 7.4. In certain embodiments, the agonists are non-cationic at a pH of about 7.2, or at a pH of about 7.3, or at a pH of about 7.4. In certain embodiments, a major portion of the present agonists in the compositions and/or drug delivery systems are non-cationic at the recited pHs or pH ranges. For example, about 90%, or about 80%, or about 70%, or about 60%, or about 50% of the agonists may be non-cationic at the recited pHs or pH ranges.

When the present alpha 2 adrenergic receptor agonists are organic cations (e.g., organic molecules having a transient or permanent positive net charge), the agonists may have a basic functionality with a pKa of less than about 7. Certain agonists may have a pKa of about 6.5, or about 6, or about 5.5, or about 5.

Additional alpha 2 adrenergic receptor agonists in accordance with the present disclosure include alpha 2 adrenergic receptor agonists that have no ionizable groups. Other additional alpha 2 adrenergic receptor agonists may have only acidic functionalities, as compared to basic functionalities. Acidic functionalities may be provided by coupling or associating one or more acidic moieties with an alpha 2 adrenergic receptor agonist base structure.

One example of an N-Mannich base prodrug is provided below as compound A.

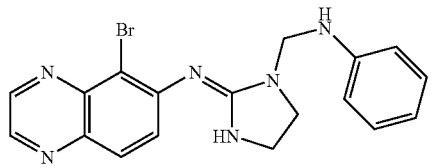

This N-Mannich base prodrug will have a pKa of 6.9, thus having a much higher fraction of uncharged species. Chemical decomposition back to brimonidine can occur. Optimizing the rate of decomposition back to brimonidine may result in an appropriate vitreous half-life.

An example of a sulfonyl prodrug is provided below as compound B:

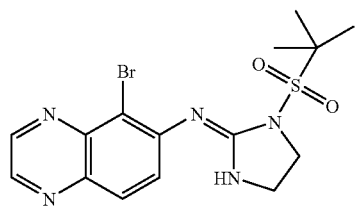

The rate of chemical hydrolysis of the sulfonyl prodrugs back to brimonidine can be optimized by judicious selection of sulfonyl moiety. The sulfonyl prodrug will have a pKa of 5 and will be uncharged at physiologic pH.

Another example of the present alpha 2 adrenergic receptor agonists include agents that activate alpha 2 adrenergic receptors and that are neutral at a physiological pH. For example, the alpha 2 adrenergic receptor agonist is not a cation at a physiological pH, such as at the pH of the interior of an eye of a human. One example of such an agonist is provided below as compound C.

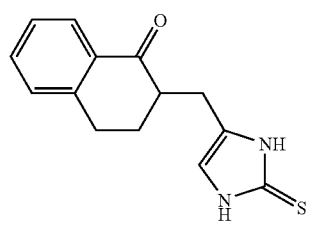

Another example of such an alpha 2 adrenergic receptor agonist is provided below as compound D

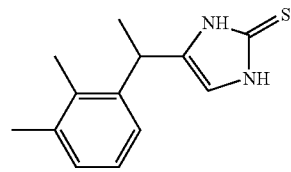

Another example of such an alpha 2 adrenergic receptor agonist is provided below as compound E

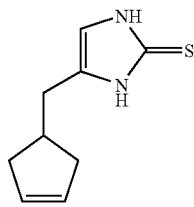

Anteriorly cleared alpha 2 adrenergic receptor agonists can be identified and obtained using standard pharmacokinetic experiments and conventional methods that are routine to persons of ordinary skill in the art. For example, potential anteriorly cleared alpha 2 adrenergic receptor agonists can be produced using conventional chemical synthesis techniques, such as techniques suitable for producing conventional alpha 2 adrenergic receptor agonists, such as brimonidine, xylazine, medetomidine, ketamine, clonidine, apraclonidine, and the like. If desired, the alpha 2 adrenergic receptor agonist can be modified or engineered, as described above. The alpha 2 adrenergic receptor agonist activity can be examined using conventional screening assays for testing conventional alpha 2 adrenergic receptor agonists. Such screening assays are routine to persons of ordinary skill in the art.

Potential anteriorly cleared alpha 2 adrenergic receptor agonists can be screened by injecting the potential agonist into a rabbit vitreous. The vitreous humor and aqueous humor can be sampled as a function of time, and the amount of the potential agonist in the vitreous and aqueous humor can be measured. The vitreous concentration of the potential agonist can be plotted as a function of time, and using standard pharmacokinetic techniques, the vitreous half-life for the potential agonist and clearance of the potential agonist can be calculated. Similarly, the aqueous concentration of the potential agonist can be plotted as a function of time, and standard pharmacokinetic techniques can be used to determine the anterior clearance of the potential agonists. Agents with desired vitreal half-lives and/or that are measurable in the aqueous humor may be used in the present materials. For example, agents that have vitreous half-lives greater than about three hours can be selected for the present ophthalmically therapeutic materials.

Compounds that have a short vitreal half-life (e.g., less than about three hours), are likely eliminated from the eye via a posterior route across the retina (Cunha-Vaz et al., "The active transport of fluoroscein by the retinal vessels and the retina", J. Physiol., 191:467-486 (1967); Barza et al., "The effects of infection and probenecid on the transport of carbenicillin from the rabbit vitreous humor", Invest Ophthalmol Vis. Sci., 22:720-726 (1982); Miller et al., "Fleroxacin pharmacokinetics in aqueous and vitreous humors determination by using complete concentration-time data from individual rabbits", Antimicrob. Agents. Chemother., 36:32-38 (1992); Cunha-Vaz, "The blood-ocular barriers", Surv. Ophthalmol., 5:279-296 (1979); Maurice et al., "Handbook of Experimental Pharmacology: Pharmacology of the Eye", Sears, Eds., Vol. 69, (Springer-Verlag, Berlin-Heidelberg), 19-116 (1986); and Lesar et al., "Antimicrobial drug delivery to the eye", Drug Intell Clin. Pharm., 19:642-654 (1985)).

Because of the large surface are of the retina available for exchanges between the vitreous and plasma, strict anterior diffusion of molecules does not occur for compounds able to cross the retina and the retinal pigment epithelium (RPE). Instead, the compounds will radially diffuse from an initial concentration distribution followed by elimination from the vitreous across the retina (e.g., the trans-retinal or posterior elimination route). Additionally, a low aqueous humor/vitreous humor concentration ratio for the compound is further evidence of a trans-retinal mechanism of elimination for such compounds (Maurice, "The exchange of sodium between the vitreous body and the blood and aqueous humor", J. Physiol, 137:119-125 (1957); and Maurice, "Protein dynamics in the eye studied with labelled proteins", Am J Ophthalmol, 49:361-367 (1959)).

In comparison, compounds eliminated by the anterior chamber route will develop an aqueous humor/vitreous humor concentration ratio that correlates well with their molecular weight (Maurice et al., "Handbook of Experimental Pharmacology: Pharmacology of the Eye", Sears, Eds., Vol. 69, (Springer-Verlag, Berlin-Heidelberg), 19-116 (1986)). Examples of compounds that are cleared by the anterior route include albumin, gentamicin, streptomycin, sulfacetamide tobramycin, kanamycin, as well as other macromolecules and peptides. It is important to note that such compounds are not alpha 2 adrenergic receptor compounds.

In view of the above, one embodiment of the present invention, relates to an ophthalmically therapeutic material that comprises a therapeutic component which comprises a therapeutically effective amount of an alpha 2 adrenergic receptor agonist having a structure effective in providing elimination of the agonist from the anterior chamber of an eye to which the agonist is administered. For example, the ophthalmically therapeutic material comprises an alpha 2 adrenergic receptor agonist that is cleared via the anterior route (e.g., through the trabecular meshwork outflow and/or the uveoscleral outflow) compared to being cleared solely through the posterior route (e.g., through the retina).

The alpha 2 adrenergic receptor agonist of the present materials is provided in an amount effective in providing one or more therapeutic effects. For example, a material may comprise an amount of an anteriorly cleared alpha 2 adrenergic receptor agonist that provides neuroprotection to the neurons in an eye, a reduction in elevated intraocular pressure, and combinations thereof. As another example, the anteriorly cleared alpha 2 adrenergic receptor agonists may be provided in amounts that are effective in treating glaucoma. In certain materials, such as the polymeric drug delivery systems described herein, the anteriorly cleared alpha 2 adrenergic receptor agonist may be released from the drug delivery system in such therapeutically effective amounts.

Some of the present materials comprise an alpha 2 adrenergic receptor agonist that has an intravitreal half-life after solution dosing greater than about three hours. For example, certain materials comprises an anteriorly cleared alpha 2 adrenergic receptor agonist that has an intravitreal half life of 4 hours, or 5 hours, or 10 hours, or 15 hours, or more. Half-life determination of such agonists can be determined as described herein.

The alpha 2 adrenergic receptor agonist of the present materials may be associated with a bulking agent, as described herein. For example, an alpha 2 adrenergic receptor agonist may be coupled to a polyethylene glycol (PEG). In certain embodiments, the alpha 2 adrenergic receptor agonist has a molecular weight greater than the molecular weight of a different alpha 2 adrenergic receptor agonist that is eliminated from the posterior segment of an eye (e.g., via the trans-retinal route).

As discussed herein, the alpha 2 adrenergic receptor agonists of the present materials may have substantially equal anterior and posterior clearance rates, or may have an enhanced anterior clearance rate relative to the posterior clearance rate. In some materials, the anterior clearance rate is less than the posterior clearance rate, but the alpha 2 adrenergic receptor agonist has an anterior clearance rate that is effective in permitting the alpha 2 adrenergic receptor agonist to be measured above a quantitation limit in the aqueous humor of an eye to which it has been administered.

The present materials are ophthalmically acceptable. Thus, the present materials can be administered to an eye of an individual without substantial negative or adverse side effects. In certain materials, the alpha 2 adrenergic receptor agonist is delivered to the anterior chamber, the posterior chamber, or a combination of the anterior chamber and posterior chamber when the material is administered to the eye.

As discussed herein, the present materials can be produced by a variety of methods. In one embodiment, the ophthalmically therapeutic material comprises a therapeutic component produced by a process comprising a step of selecting an alpha 2 adrenergic receptor agonist that has a vitreous half-life greater than about three hours. Methods of determining the vitreous half-life of such agonists are described herein. Other embodiments may comprise selecting an agonist that has a vitreous half-life of about 4 hours, or 5 hours, or 10 hours, or 15 hours, or more.

In certain embodiments, the present materials comprise a therapeutic component produced by a process comprising administering an alpha-2 adrenergic receptortagonist to an eye of a subject; determining the concentration of the alpha-2 adrenergic receptor agonist in the vitreous body or vitreous humor and/or aqueous humor as a function of time; determining the vitreous half-life and/or clearance of the alpha-2 adrenergic receptor agonist; and combining the alpha-2 adrenergic receptor agonist with at least one other component useful in the present materials if the half-life of the alpha-2 adrenergic receptor agonist is greater than about three hours. In situations where modeling methods may be used, some of the foregoing steps used to produce the therapeutic component may be changed or omitted. Thus, the therapeutic component may be produced by a process comprising determining whether the half-life of the alpha-2 adrenergic receptor agonist is greater than about three hours, and if so, combining the alpha-2 adrenergic receptor agonist with one or more components or component precursors of the compositions or polymeric drug delivery systems. The half-life may specifically be understood to be the intravitreal half-life after solution dosing of the alpha-2 adrenergic receptor agonist.

The present materials may also include salts of the anteriorly cleared alpha 2 adrenergic receptor agonist or other therapeutic agents when appropriate. Pharmaceutically acceptable acid addition salts are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

As discussed herein, the present materials may be understood to be liquid-containing compositions. Thus, certain of the present materials may comprise a liquid carrier component associated with the therapeutic component in the form of a composition suitable for administration to a patient by intravitreal administration and/or periocular administration. As used herein, periocular administration refers to delivery of the therapeutic component to a retrobulbar region, a subconjunctival region, a subtenon region, a suprachoroidal region or space, and/or an intrascleral region or space. For example, an anteriorly cleared alpha 2 adrenergic receptor agonist may be associated with water, saline, phosphate buffer, or other ophthalmically acceptable liquid carrier. The present liquid-containing compositions are preferably in an injectable form. In other words, the compositions may be intraocularly administered, such as by intravitreal injection, using a syringe and needle or other similar device (e.g., see U.S. Patent Publication No. 2003/0060763), or the compositions can be periocularly administered using an injection device.

The therapeutic component of the present compositions may be present in an amount in the range of about 1% or less to about 5% or about 10% or about 20% or about 30% or more (w/v or w/w) of the composition. For intravitreally administered compositions, providing relatively high concentrations or amounts of the therapeutic component in the present compositions may be beneficial in that reduced amounts of the composition may be required to be placed or injected into the posterior segment of the eye in order to provide the same amount or more of the therapeutic component in the posterior segment of the eye relative to other compositions.

In certain embodiments, the material further comprises an excipient component. The excipient component may be understood to include solubilizing agents, viscosity inducing agents, buffer agents, tonicity agents, preservative agents, and the like.

In some embodiments of the present compositions, a solubilizing agent may be a cyclodextrin. In other words, the present materials may comprise a cyclodextrin component provided in an amount from about 0.1% (w/v) to about 5% (w/v) of the composition. In further embodiments, the cyclodextrin comprises up to about 10% (w/v) of certain cyclodextrins, as discussed herein. In further embodiments, the cyclodextrin comprises up to about 60% (w/v) of certain cyclodextrins, as discussed herein. The excipient component of the present compositions may comprise one or more types of cyclodextrins or cyclodextrin derivatives, such as alpha-cyclodextrins, beta-cyclodextrins, gamma-cyclodextrins, and derivatives thereof. As understood by persons of ordinary skill in the art, cyclodextrin derivatives refer to any substituted or otherwise modified compound that has the characteristic chemical structure of a cyclodextrin sufficiently to function as a cyclodextrin, for example, to enhance the solubility and/or stability of therapeutic agents and/or reduce unwanted side effects of the therapeutic agents and/or to form inclusive complexes with the therapeutic agents.

Viscosity inducing agents of the present materials, include without limitation, polymers that are effective in stabilizing the therapeutic component in the composition. The viscosity inducing component is present in an effective amount in increasing, advantageously substantially increasing, the viscosity of the composition. Increased viscosities of the present compositions may enhance the ability of the present compositions to maintain the therapeutic component, including therapeutic component particles, in substantially uniform suspension in the compositions for prolonged periods of time, for example, for at least about one week, without requiring resuspension processing. The relatively high viscosity of the present compositions may also have an additional benefit of at least assisting the compositions to have the ability to have an increased amount or concentration of the therapeutic component, as discussed elsewhere herein, for example, while maintaining such therapeutic component in substantially uniform suspension for prolonged periods of time.

Any suitable viscosity inducing component, for example, ophthalmically acceptable viscosity inducing component, may be employed in the present compositions. Many such viscosity inducing components have been proposed and/or used in ophthalmic compositions used on or in the eye. The viscosity inducing component is present in an amount effective in providing the desired viscosity to the composition. Advantageously, the viscosity inducing component is present in an amount in a range of about 0.5% or about 1.0% to about 5% or about 10% or about 20% (w/v or w/w) of the composition. The specific amount of the viscosity inducing component employed depends upon a number of factors including, for example and without limitation, the specific viscosity inducing component being employed, the molecular weight of the viscosity inducing component being employed, the viscosity desired for the present composition being produced and/or used and the like factors.

The viscosity inducing component preferably comprises a polymeric component and/or at least one viscoelastic agent, such as those materials which are useful in ophthalmic surgical procedures. Examples of useful viscosity inducing components include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

The molecular weight of the presently useful viscosity inducing components may be in a range of about 10,000 Daltons or less to about 2 million Daltons or more. In one particularly useful embodiment, the molecular weight of the viscosity inducing component is in a range of about 100,000 Daltons or about 200,000 Daltons to about 1 million Daltons or about 1.5 million Daltons. Again, the molecular weight of the viscosity inducing component useful in accordance with the present invention, may vary over a substantial range based on the type of viscosity inducing component employed, and the desired final viscosity of the present composition in question, as well as, possibly one or more other factors.

If desired, buffering agents may be provided in an amount effective to control the pH of the composition. Tonicity agents may be provided in an amount effective to control the tonicity or osmolality of the compositions. Certain of the present compositions include both a buffer component and a tonicity component, which may include one or more sugar alcohols, such as manitol, or salts, such as sodium chloride, as discussed herein. The buffer component and tonicity component may be chosen from those which are conventional and well known in the ophthalmic art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, any other suitable ophthalmically acceptably tonicity component and mixtures thereof.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

Preservative agents that may be used in the present materials include benzyl alcohol, benzalkonium chloride, methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

The present compositions can be produced using conventional techniques routinely known by persons of ordinary skill in the art. For example, a therapeutic component can be combined with a liquid carrier. The composition can be sterilized. In certain embodiments, such as preservative-free embodiments, the compositions can be sterilized and packaged in single-dose amounts. The compositions may be prepackaged in intraocular dispensers which can be disposed of after a single administration of the unit dose of the compositions.

The present compositions can be prepared using suitable blending/processing techniques, for example, one or more conventional blending techniques. The preparation processing should be chosen to provide the present compositions in forms which are useful for intravitreal or periocular placement or injection into eyes of humans or animals. In one useful embodiment a concentrated therapeutic component dispersion is made by combining the therapeutic component with water, and the excipients (other than the viscosity inducing component) to be included in the final composition. The ingredients are mixed to disperse the therapeutic component and then autoclaved. The viscosity inducing component may be purchased sterile or sterilized by conventional processing, for example, by filtering a dilute solution followed by lyophylization to yield a sterile powder. The sterile viscosity inducing component is combined with water to make an aqueous concentrate. The concentrated therapeutic component dispersion is mixed and added as a slurry to the viscosity inducing component concentrate. Water is added in a quantity sufficient (q.s.) to provide the desired composition and the composition is mixed until homogenous.

In one embodiment, a sterile, viscous, suspension suitable for administration is made using an anteriorly cleared alpha 2 adrenergic receptor agonist. A process for producing such a composition may comprise sterile suspension bulk compounding and aseptic filling.

Other embodiments of the present materials are in the form of a polymeric drug delivery system that is capable of providing sustained drug delivery for extended periods of time after a single administration. For example, the present drug delivery systems can release the anteriorly cleared alpha 2 adrenergic receptor agonist for at least about 1 month, or about 3 months, or about 6 months, or about 1 year, or about 5 years or more. Thus, such embodiments of the present materials may comprise a polymeric component associated with the therapeutic component in the form of a polymeric drug delivery system suitable for administration to a patient by at least one of intravitreal administration and periocular administration.

The polymeric drug delivery system may be in the form of biodegradable polymeric implants, non-biodegradable polymeric implants, biodegradable polymeric microparticles, and combinations thereof. Implants may be in the form of rods, wafers, sheets, filaments, spheres, and the like. Particles are smaller than the implants disclosed herein, and may vary in shape. For example, certain embodiments of the present invention utilize substantially spherical particles. These particles may be understood to be microspheres. Other embodiments may utilize randomly configured particles, such as particles that have one or more flat or planar surfaces. The drug delivery system may comprise a population of such particles with a predetermined size distribution. For example, a major portion of the population may comprise particles having a desired diameter measurerment.

As discussed herein, the polymeric component of the present drug delivery systems can comprise a polymer selected from the group consisting of biodegradable polymers, non-biodegradable polymers, biodegradable copolymers, non-biodegradable copolymers, and combinations thereof. In certain embodiments, the polymeric component comprises a poly (lactide-co-glycolide) polymer (PLGA). In other embodiments, the polymeric component comprises a polymer selected from the group consisting of poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, derivatives thereof, and combinations thereof. The polymeric component may be associated with the therapeutic component to form an implant selected from the group consisting of solid implants, semisolid implants, and viscoelastic implants.

The anteriorly cleared alpha 2 adrenergic receptor agonist may be in a particulate or powder form and entrapped by a biodegradable polymer matrix. Usually, anteriorly cleared alpha 2 adrenergic receptor agonist particles in intraocular implants will have an effective average size less than about 3000 nanometers. However, in other embodiments, the particles may have an average maximum size greater than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers. In addition, when such particles are combined with a polymeric component, the resulting polymeric intraocular particles may be used to provide a desired therapeutic effect.

The anteriorly cleared alpha 2 adrenergic receptor agonist of the present systems is preferably from about 1% to 90% by weight of the drug delivery system. More preferably, the anteriorly cleared alpha 2 adrenergic receptor agonist is from about 20% to about 80% by weight of the system. In a preferred embodiment, the anteriorly cleared alpha 2 adrenergic receptor agonist comprises about 40% by weight of the system (e.g., 30%-50%). In another embodiment, the anteriorly cleared alpha 2 adrenergic receptor agonist comprises about 60% by weight of the system.

Suitable polymeric materials or compositions for use in the drug delivery systems include those materials which are compatible, that is biocompatible, with the eye so as to cause no substantial interference with the functioning or physiology of the eye. Such materials preferably include polymers that are at least partially and more preferably substantially completely biodegradable or bioerodible.

In addition to the foregoing, examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present drug delivery systems.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present systems may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Also important to controlling the biodegradation of the polymer and hence the extended release profile of the drug delivery systems is the relative average molecular weight of the polymeric composition employed in the present systems. Different molecular weights of the same or different polymeric compositions may be included in the systems to modulate the release profile. In certain systems, the relative average molecular weight of the polymer will range from about 9 to about 64 kD, usually from about 10 to about 54 kD, and more usually from about 12 to about 45 kD.

In some drug delivery systems, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the system, where a more flexible system or implant is desirable for larger geometries. The % of polylactic acid in the polylactic acid polyglycolic acid (PLGA) copolymer can be 0-100%, preferably about 15-85%, more preferably about 35-65%. In some systems, a 50/50 PLGA copolymer is used.

The biodegradable polymer matrix of the present systems may comprise a mixture of two or more biodegradable polymers. For example, the system may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. It may be understood that the polymeric component of the present systems is associated with the therapeutic component so that the release of the therapeutic component into the eye is by one or more of diffusion, erosion, dissolution, and osmosis. As discussed herein, the matrix of an intraocular drug delivery system may release drug at a rate effective to sustain release of an amount of the anteriorly cleared alpha 2 adrenergic receptor agonist for more than one week after implantation into an eye. In certain systems, therapeutic amounts of the anteriorly cleared alpha 2 adrenergic receptor agonist are released for more than about one month, and even for about twelve months or more. For example, the therapeutic component can be released into the eye for a time period from about ninety days to about one year after the system is placed in the interior of an eye.

The release of the anteriorly cleared alpha 2 adrenergic receptor agonist from the drug delivery systems comprising a biodegradable polymer matrix may include an initial burst of release followed by a gradual increase in the amount of the anteriorly cleared alpha 2 adrenergic receptor agonist released, or the release may include an initial delay in release of the anteriorly cleared alpha 2 adrenergic receptor agonist followed by an increase in release. When the system is substantially completely degraded, the percent of the anteriorly cleared alpha 2 adrenergic receptor agonist that has been released is about one hundred.

It may be desirable to provide a relatively constant rate of release of the therapeutic agent from the drug delivery system over the life of the system. For example, it may be desirable for the anteriorly cleared alpha 2 adrenergic receptor agonist to be released in amounts from about 0.01 μg to about 2 μg per day for the life of the system. However, the release rate may change to either increase or decrease depending on the formulation of the biodegradable polymer matrix. In addition, the release profile of the anteriorly cleared alpha 2 adrenergic receptor agonist may include one or more linear portions and/or one or more non-linear portions. Preferably, the release rate is greater than zero once the system has begun to degrade or erode.

The drug delivery systems, such as the intraocular implants, may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the anteriorly cleared alpha 2 adrenergic receptor agonist falls within a narrow window. In addition, the therapeutic component, including the therapeutic agent(s) described herein, may be distributed in a non-homogenous pattern in the matrix. For example, the drug delivery system may include a portion that has a greater concentration of the anteriorly cleared alpha 2 adrenergic receptor agonist relative to a second portion of the system.

The polymeric implants disclosed herein may have a size of between about 5 μm and about 2 mm, or between about 10 μm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e. g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. However, larger implants may also be formed and further processed before administration to an eye. In addition, larger implants may be desirable where relatively greater amounts of the anteriorly cleared alpha 2 adrenergic receptor agonist are provided in the implant. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Drug delivery systems can be prepared where the center may be of one material and the surface may have one or more layers of the same or a different composition, where the layers may be cross-linked, or of a different molecular weight, different density or porosity, or the like. For example, where it is desirable to quickly release an initial bolus of anteriorly cleared alpha 2 adrenergic receptor agonist, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The drug delivery systems may be of any geometry including fibers, sheets, films, microspheres, spheres, circular discs, plaques and the like. The upper limit for the system size will be determined by factors such as toleration for the system, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 μm to 4 mm in diameter, with comparable volumes for other shaped particles.

The size and form of the system can also be used to control the rate of release, period of treatment, and drug concentration at the site of implantation. For example, larger implants will deliver a proportionately larger dose, but depending on the surface to mass ratio, may have a slower release rate. The particular size and geometry of the system are chosen to suit the site of implantation.

The proportions of therapeutic agent, polymer, and any other modifiers may be empirically determined by formulating several implants, for example, with varying proportions of such ingredients. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the therapeutic component, and similar to the compositions described herein, the polymeric drug delivery systems disclosed herein may include an excipient component. The excipient component may be understood to include solubilizing agents, viscosity inducing agents, buffer agents, tonicity agents, preservative agents, and the like.

Additionally, release modulators such as those described in U.S. Pat. No. 5,869,079 may be included in the drug delivery systems. The amount of release modulator employed will be dependent on the desired release profile, the activity of the modulator, and on the release profile of the therapeutic agent in the absence of modulator. Electrolytes such as sodium chloride and potassium chloride may also be included in the systems. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

Various techniques may be employed to produce the drug delivery systems described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the drug delivery systems, and typically yield elements with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

In certain embodiments of the present invention, a method of producing a sustained-release intraocular drug delivery system, comprises combining an anteriorly cleared alpha 2 adrenergic receptor agonist and a polymeric material to form a drug delivery system suitable for placement in an eye of an individual. The resulting drug delivery system is effective in releasing the anteriorly cleared alpha 2 adrenergic receptor agonist into the eye for extended periods of time. The method may comprise a step of extruding a particulate mixture of the anteriorly cleared alpha 2 adrenergic receptor agonist and the polymeric material to form an extruded composition, such as a filament, sheet, and the like.

When polymeric particles are desired, the method may comprise forming the extruded composition into a population of polymeric particles or a population of implants, as described herein. Such methods may include one or more steps of cutting the extruded composition, milling the extruded composition, and the like.

As discussed herein, the polymeric material may comprise a biodegradable polymer, a non-biodegradable polymer, or a combination thereof. Examples of polymers include each and every one of the polymers and agents identified above.

Embodiments of the present invention also relate to compositions comprising the present drug delivery systems. For example, and in one embodiment, a composition may comprise the present drug delivery system and an ophthalmically acceptable carrier component. Such a carrier component may be an aqueous composition, for example saline or a phosphate buffered liquid.

Another embodiment of the invention relates to anteriorly cleared alpha 2 adrenergic receptor agonists. Such agonists have chemical or physical structures that are effective in providing an anterior clearance of the agonist from the eye to which they are administered. Such agonists can be administered to the eye by intravitreal or periocular administration. Such agonists can be used in the manufacture of a medicament to treat one or more ocular conditions, such as glaucoma. In certain embodiments, the agonists can be used in a medicament to treat a condition affecting the anterior segment of the eye and the posterior segment of the eye.

Another embodiment relates to a method of producing an ophthalmically therapeutic material which comprises an anteriorly cleared alpha 2 adrenergic receptor agonist. In a broad aspect, the method comprises the steps of selecting an alpha 2 adrenergic receptor agonist that has a vitreous half-life greater than about 3 hours; and combining the selected alpha 2 adrenergic receptor agonist with a liquid carrier component or a polymeric component to form a material suitable for administration to an eye. Or stated differently, a method of producing the present materials may comprise a step of selecting alpha 2 adrenergic receptor agonists having a high aqueous humor/vitreous humor concentration ratio and long intravitreal half-lifes.

The method may further comprise one or more of the following steps, which will typically be used to select the anteriorly cleared alpha 2 adrenergic receptor agonist: administering an alpha 2 adrenergic receptor agonist to an eye of a subject and determining the concentration of the alpha 2 adrenergic receptor agonist in at least one of the vitreous humor and aqueous humor as a function of time; and administering an alpha 2 adrenergic receptor agonist to an eye of a subject and determining at least one of the vitreous half-life and clearance of the alpha 2 adrenergic receptor agonist from the eye.

The material formed in the method may be a liquid-containing composition, a biodegradable polymeric implant, a non-biodegradable polymeric implant, polymeric microparticles, or combinations thereof. As discussed herein, the material may be in the form of solid implants, semisolid implants, and viscoelastic implants. In certain embodiments, the anteriorly cleared alpha 2 adrenergic receptor agonist is combined with a polymeric component to form a mixture, and the method further comprises extruding the mixture.

Additional embodiments of the present invention related to methods of improving or maintaining vision of an eye of a patient. In general, the methods comprise a step of administering the present ophthalmically therapeutic material to an eye of an individual in need thereof. Administration, such as intravitreal or periocular administration of the present materials can be effective in treating anterior ocular conditions, posterior ocular conditions, or combinations thereof. For example, certain of the present materials can be administered to a patient to provide neuroprotection to ocular neuronal cells and to reduce elevated intraocular pressure. The present materials may be particularly useful in treating glaucoma. Administration of the present materials are effective in delivering the alpha 2 adrenergic receptor agonist to one or more posterior structures of the eye including the uveal tract, the vitreous, the retina, the choroid, the retinal pigment epithelium.

The present compositions and drug delivery systems can effectively treat anterior ocular conditions, such as conditions or diseases affecting the anterior segment of an eye (including the anterior chamber and posterior chamber of the eye) when administered intraocularly into the posterior segment of an eye, or periocularly, as described above. In addition, the present compositions and drug delivery systems may also effectively treat posterior ocular conditions, such as conditions or diseases affecting the posterior segment of an eye (including the retina of the eye).

In additional embodiments, the present compositions and drug delivery systems may be administered to a patient in combination with one or more topical ophthalmic compositions. For example, the present compositions and drug delivery systems may be administered in combination with a composition effective in lowering intraocular pressure (IOP) of an eye of a patient. The present combination therapies may enhance the anterior clearance of the therapeutic agents of the present compositions and drug delivery systems. For example, by lowering the IOP of a patient, for example by about 5 mmHg, enhanced movement of the therapeutic agent towards the anterior segment of the eye can be obtained. It has been proposed that the movement of FITC-dextran from the vitreous into the aqueous was enhanced when IOP was lowered with a topical bunazosin solution applied to rabbit eyes (Sugiura et al., "Effects of intraocular pressure change on movement of FITC-dextran across vitreous-aqueous interface", (1989), Jpn J. Ophthalmol, 33(4):441-450).

Other combination therapies may include the administration of the present compositions and/or drug delivery systems in combination with surgical procedures which attempt to decrease IOP. For example, the present compositions and/or drug delivery systems can be administered in patients who have received or will be receiving trabecular meshwork surgery using a laser or mechanical surgical techniques.

Organic cations can be understood to be organic molecules having a transient or permanent positive net charge, for example at a physiological pH. Examples of organic cations include anticholinergics, adrenergics, antineoplastics, sympathomimetics, antihistamines, xenobiotics, some vitamins, and a variety of endogenous amines, such as choline, epinephrine, dopamine, and guanidine. Such organic cations can be transported across barriers or membranes by organic cation transporters. Inhibition, including competitive inhibition and non-competitive inhibition, can reduce the transport of organic cations using organic cation transporters.

Thus, additional combination therapies may include administration of the present compositions and/or drug delivery systems in combination with administration of an RPE organic cation transporter inhibitor. For example, administration of an RPE organic cation transporter inhibitor may decrease the posterior transport rate of the present alpha 2 adrenergic receptor agonists and thereby cause an increase in intravitreal half-life of the alpha 2 adrenergic receptor agonists and an associated increase or enhancement in anterior clearance rate. Examples of suitable RPE organic cation transporter inhibitors include metabolic inhibitors and organic cations. Examples of metabolic ihhibitiors include, without limitation, carbonylcyanide-p-(trifluoromethoxy) phenylhydrazone, 2,4-dinitrophenol, $NaN_3$, rotenone, and $HgCl_2$. Competitive inhibition can occur with organic cations. Examples of organic cations include, without limitation, quinacrine, pyrilamine, quinidine, valinomycin, diprivefrine, carbachol, diphenylhydramine, diltiazem, timolol, propanolol, and verapamil. Such inhibitors are useful in inhibiting transport of verapamil in human RPE cell lines (Han et al., "Characterization of a Novel Cationic Drug Transporter in Human Retinal Pigment Epithelial Cells", Journal of Pharmacology and Experimental Therapeutics, 296(2): 450-457, 2001). Other inhibitiors include cimetidine, which is a high affinity inhibitor of organic cation transporter 2 (OCT2), and tyrosine, which is a high affinity inhibitor of OCT1. In certain embodiments, the present alpha 2 adrenergic receptor agonists can be administered to an eye of a patient in combination with an alpha 2 adrenergic receptor agonist that is present as a cation at physiological pHs. For example, the present alpha 2 adrenergic receptor agonists can be administered in conjunction with brimonidine. Such cationic alpha 2 adrenergic receptor agonists can competitively inhibit organic cation transport of the present alpha 2 adrenergic receptor agonists.

The RPE organic cation transporter inhibitors can be administered separately from the present alpha 2 adrenergic receptor agonists, or can be administered in combination with the present agonists. Thus, the combination therapy may include administration of a single composition or polymeric drug delivery system comprising the present alpha 2 adrenergic receptor agonists and one or more RPE organic cation transporter inhibitors.

When a syringe apparatus is used to administer the present materials, the apparatus can include an appropriately sized needle, for example, a 27 gauge needle or a 30 gauge needle. Such apparatus can be effectively used to inject the materials into the posterior segment or a periocular region of an eye of a human or animal. The needles may be sufficiently small to provide an opening that self seals after removal of the needle.

The present methods may comprise a single injection into the posterior segment of an eye or may involve repeated injections, for example over periods of time ranging from about one week or about 1 month or about 3 months to about 6 months or about 1 year or longer.

The present materials are preferably administered to patients in a sterile form. For example, the present materials may be sterile when stored. Any routine suitable method of sterilization may be employed to sterilize the materials. For example, the present materials may be sterilized using radiation. Preferably, the sterilization method does not reduce the activity or biological or therapeutic activity of the therapeutic agents of the present systems.

The materials can be sterilized by gamma irradiation. As an example, the drug delivery systems can be sterilized by 2.5 to 4.0 mrad of gamma irradiation. The drug delivery systems can be terminally sterilized in their final primary packaging system including administration device e.g. syringe applicator.

Alternatively, the drug delivery systems can be sterilized alone and then aseptically packaged into an applicator system. In this case the applicator system can be sterilized by gamma irradiation, ethylene oxide (ETO), heat or other means. The drug delivery systems can be sterilized by gamma irradiation at low temperatures to improve stability or blanketed with argon, nitrogen or other means to remove oxygen. Beta irradiation or e-beam may also be used to sterilize the implants as well as UV irradiation. The dose of irradiation from any source can be lowered depending on the initial bioburden of the drug delivery systems such that it may be much less than 2.5 to 4.0 mrad. The drug delivery systems may be manufactured under aseptic conditions from sterile starting components. The starting components may be sterilized by heat, irradiation (gamma, beta, UV), ETO or sterile filtration. Semi-solid polymers or solutions of polymers may be sterilized prior to drug delivery system fabrication and anteriorly cleared alpha 2 adrenergic receptor agonist incorporation by sterile filtration of heat. The sterilized polymers can then be used to aseptically produce sterile drug delivery systems.

In addition to the anteriorly cleared alpha 2 adrenergic receptor agonist included in the present ophthalmically therapeutic materials disclosed hereinabove, the materials may also include one or more additional ophthalmically acceptable therapeutic agents. For example, an ophthalmically therapeutic material may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof.

Examples of additional pharmacologic or therapeutic agents which may find use in the present materials, include, without limitation, those disclosed in U.S. Pat. Nos. 4,474,451, columns 4-6 and 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, aziocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, fluocinolone, triamcinolone, triamcinolone acetonide, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppresive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phosphonoformic acid, ganciclovir and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, Ginkgo Biloba extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof.

The present materials are configured to release an amount of the anteriorly cleared alpha 2 adrenergic receptor agonist effective to treat or reduce a symptom of an ocular condition, such as an ocular condition such as glaucoma.

The materials disclosed herein may also be configured to deliver-additional therapeutic agents, as described above, which to prevent diseases or conditions, such as the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis and Uveitis Syndrome, Vogt-Koyanagi-Harada Syndrome.

VASCULAR DISEASES/EXUDATIVE DISEASES: Coat's Disease, Parafoveal Telangiectasis, Papillophlebitis, Frosted Branch Angitis, Sickle Cell Retinopathy and other Hemoglobinopathies, Angioid Streaks, Familial Exudative Vitreoretinopathy.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy, Retinopathy of Prematurity (retrolental fibroplastic).

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Systemic Disorders with Accosiated Retinal Dystrophies, Congenital Stationary Night Blindness, Cone Dystrophies, Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum, Osler Weber syndrome.

RETINAL TEARS/HOLES: Retinal Detachment, Macular Hole, Giant Retinal Tear.

TUMORS: Retinal Disease Associated with Tumors, Solid Tumors, Tumor Metastasis, Benign Tumors, for example, hemangiomas, neurofibromas, trachomas, and pyogenic granulomas, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis, Ocular inflammatory and immune disorders, ocular vascular malfunctions, Corneal Graft Rejection, Neovascular Glaucoma and the like.

In another aspect of the invention, kits for treating an ocular condition of the eye are provided, comprising: a) a container, such as a syringe or other applicator, comprising an anteriorly cleared alpha 2 adrenergic receptor agonist as herein described; and b) instructions for use. Instructions may include steps of how to handle the material, how to insert the material into an ocular region, and what to expect from using the material. The container may contain a single dose of the anteriorly cleared alpha 2 adrenergic receptor agonist.

EXAMPLES

The following non-limiting examples provide those of ordinary skill in the art with specific preferred drug delivery systems, methods of making such systems, and methods to treat conditions within the scope of the present invention. The following examples are not intended to limit the scope of the invention.

Example 1

Intravitreal Clearance of Brimonidine

Intravitreal clearance of brimonidine was examined in albino rabbits. Rabbits were dosed bilaterally via a 50 microliter intravitreal injection of a solution containing 928 nanograms of brimonidine. Vitreous humor samples were collected at different time points and the brimonidine concentration in the vitreous humor was determined.

As shown in FIG. 1, the vitreal concentration of brimonidine declined exponentially from 608±116 ng/mL at 0.5 hours post dose to 9.68±6.48 ng/mL at 10 hours post dose. The estimated vitreous half-life ($t_{1/2}$) of brimonidine was determined to be 1.45 hours. The vitreal clearance rate was estimated to be 0.487 mL/hour.

Based on these results, it was concluded that brimonidine is eliminated from the vitreous by a trans-retinal route. These results demonstrate that hydrophilic to moderately lipophilic alpha 2 adrenergic receptor agonists having a trans-retinal route of clearance from the posterior segment of the eye, cannot be effectively delivered to the anterior and/or posterior chambers of the eye via intravitreal administration.

Example 2

Pharmacokinetic Properties of Brimonidine Intravitreal Implants

Biodegradable polymeric implants containing brimonidine were prepared in accordance with the methods described herein. The implants were made from polylactic acid (PLA) and included 200 micrograms of brimonidine. These brimonidine implants were administered to the vitreous of rabbit eyes. Vitreous humor and aqueous humor samples were obtained at various time points, and the amount of brimonidine was determined in the samples, as shown in Table 1 below

TABLE 1

| | Brimonidine Concentration | | | | |
|---|---|---|---|---|---|
| Day | Aqueous Humor (ng/mL) | Iris-ciliary body (ng/g) | Lens (ng/g) | Retina (ng/g) | Vitreous humor (ng/mL) |
| 8 | NC | 942 (3010)[d] | 45.1 ± 13.4 | 3630 ± 2111 | 47.2 ± 13.1 |
| 31 | NC | 25.9 ± 9.11 | 17.0 ± 3.92 | 35.3 ± 15.5 | 9.35 ± 6.25[b] |
| 58 | NC | 69.4 ± 55.3 | 17.9 ± 12.5[b] | 122 ± 57.3[a] | 5.6 ± 3.24[b] |
| 91 | NC | 42.9 ± 18.7[c] | 50.1 ± 14.8 | 488 ± 471[b] | 59.3 ± 43.2 |
| 136 | NC | 107 ± 41.5 | 16.2 ± 12.3[a] | 22.6 ± 5.9 | NC |
| 184 | NC | NC | 1.18 ± 0.71[b] | 59.8 ± 35.0[b] | NC |

In Table 1, NC means "not calculable" because greater than 50% of concentrations contributing to the mean were BLQ (below the limit of quantitation).
The data are expressed as the mean ± SEM (N = 4 eyes and N = 2 plasma per sampling time).
In addition, the letters a, b, c, and d are defined as follows:
[a]N = 4. One sample was BLQ (included in the mean calculation as 0).
[b]N = 4. Two samples were BLQ (included in the mean calculation as 0).
[c]N = 3. One sample was not detectable (ND).
[d]N = 2. Two samples were above the limit of quantitation (estimated mean value in parentheses).

The $EC_{50}$ for brimonidine to activate the alpha 2 adrenergic receptor in isolated assay systems is about 2 nM. Based on doubling this as a target concentration ($C_{ss}$) and the vitreal clearance (Cl) a constant delivery of 2.5 µg of brimonidine at 0.57 ng/hour ($R_o$) is desirable for intravitreal implant devices to maintain the desired steady state drug level for a duration of six months using the following equation: $R_o=C_{ss}*Cl$.

Unexpectedly, as shown in Table 1, when the brimonidine implants were implanted in the vitreous, the implants released brimonidine to provide high vitreous and retinal concentrations of brimonidine that were maintained over a long period of time but only provided low or undetectable amounts of brimonidine in the aqueous humor. Thus, the brimonidine implants resulted in therapeutic levels of brimonidine at the retina for neuroprotection, but not in the anterior chamber. Thus, it was concluded that brimonidine when administered intravitreally can provide a neuroprotective effect, but may not provide a reduction in intraocular pressure associated with effects in the anterior segment of the eye.

Example 3

Pharmacokinetic Properties of Brimonidine Subconjunctival Administered to an Eye Brimonidine was administered to the subconjunctiva of New Zealand White rabbits by implantation of a polylactic acid (PLA) wafer containing 250 µg of brimonidine, a poly-ortho-ester (POE) rod containing 200 µg of brimonidine, or a single 100 µL injection containing 20 µg or 200 µg of brimonidine PLA microspheres. A 100 µL injection of 10 mg/mL of micropsheres (20 µg brimonidine) contained 98% (w/w) of PLA polymer having an inherent viscosity of 0.6 dl/g (i.e., 980 µg of PLA) and 2% (w/w) of brimonidine free base (i.e., 20 µg). A less than or equal to 100 µL or 200 µL injection of 100 mg/mL or 200 mg/mL microspheres, respectively (200 µg brimonidine) contained 98% (w/w) of PLA polymer having an inherent viscosity of 0.6 dL/g (i.e. 9.8 mg of PLA), and 2% (w/w) of brimonidine free base (i.e., 200 µg). A 1 mg waver containing 250 µg brimonidine contained 75% (w/w) PLA (R206) polymer (750 µg), and 25% (w/w) of brimonidine tartrate (250 µg). A 1 mg rod containing 250 µg of brimonidine contained 80% (w/w) of APF 255 POE (APF94) polymer (800 µg) and 20% (w/w) of brimonidine (200 µg). A 1 mg rod containing 200 µg of brimonidine contained 80% (w/w) of APF 260 POE (APF99) polymer (800 µg) and 20% (w/w) of brimonidine (200 µg). A 1 mg rod containing 200 µg of brimonidine contained 80% (w/w) of APF 423 POE (APF162) polymer (800 µg) and 20% (w/w) of brimonidine (200 µg).

Thirty groups of rabbits (2 rabbits per group) were used. The groups were divided into 6 sections of 5 groups. One section received 10 mg/mL of microspheres containing 20 µg of brimonidine, one section received 100 mg/mL of microspheres containing 200 µg of brimonidine, one section received 1 mg POE-AP94 implants containing 200 µg of brimonidine, one section received 1 mg POE-AP99 implants containing 200 µg of brimonidine, one section received 1 mg POE-AP162 implants containing 200 µg of brimonidine, and one section received 1 mg PLA wafers containing 250 µg of brimonidine. In each section, one group underwent ophthalmic observation at 5 days after dosing (DAD) and were euthanized at 8 DAD, one group underwent ophthalmic observation at 5 and 29 DAD and were euthanized at 31 DAD, one group underwent ophthalmic observation at 5, 29, and 54 DAD and were euthanized at 60 DAD, and two groups underwent ophthalmic observation at 5, 29, 54, and 86 DAD and were euthanized at 93 DAD. The drug delivery systems were formulated to provide a 10-20 nM (3-6 ng/mL) brimonidine target concentration since the at least 2 nM of brimonidine are required to provide optic neuroprotection.

The dose of brimonidine was based on a vitreal clearance rate of 0.487 ml/day and a target therapeutic concentration for brimonidine. Based on the relationship $C_{ss}=R_o/Cl$, where $R_o$=delivery rate, $C_{ss}$=steady-state concentration, and Cl=vitreal clearance, the release rate over a 3 month period of time was calculated to be about 1.46-2.92 ng/day. The 10 mg/mL and 100 mg/mL microspheres provided release rates of 1.4 and 14 µg/day for 60 days. The APF255, APF260, and APF423 provided release rates of about 2.2, 2.6, and 2.5 µg/day, respectively. The PLA wafer provided a release rate of about 5 µg/day over 30 days and 1.25 µg/day out to 90 days. A single implant was sufficient, and conventional methods were used to determine intraocular and systemic pharmacokinetics.

Eyes were prepared for surgery by topical application of two drops of 1% tropicamide and two drops of phenylephrine hydrochloride 2.5%. Betadine was applied and washed from the eyes, and 1-2 drops of 0.5% proparacaine hydrochloride were delivered to each eye. After a 3 mm conjunctival incision was made extending from the limbus and lateral to the dorsal rectus muscle, a single subconjunctival injection or implantation of a brimonidine drug delivery system was made. Rods and wafers were administered using forceps. Conjunctivae were sutured closed and received a ocular lubricant. Subconjunctival injections were performed by elevating the bulbar conjunctiva in the dorsotemporal quadrant using forceps. An injection was made into the subconjunctival space.

Gross ocular examinations were performed once weekly and during the first week, more thorough ophthalmic examinations (slit lamp and indirect ophthalmoscopy) were performed instead. The examinations included observations of the eyelids, conjunctiva, cornea, anterior chamber, iris, lens, vitreous, and retina. Intraocular pressure (IOP) was recorded at 8 am, 12 noon and 4 µm using a Medtronic Solan, Model 30 classic pneumatonometer on conditioned rabbits. Tear tissue, aqueous humor tissue, and remaining tissues were collected and stored.

Based on gross ocular examinations, no conjunctival congestion, swelling, or discharge was observed.

Based on slit lamp and indirect ophthalmoscopy, an insignificant number of eyes exhibited conjunctival congestion. A minor number of eyes were observed to have cataracts that were concluded to not be drug-related. Conjunctival pigmentation was observed in some eyes, and was not considered to be of toxicological significance. Similarly, some eyes exhibited increased vascularization which was not considered to be toxicocologically significant.

At day 14, the mean IOP fore eyes treated with APF 423 POE implants (200 µg brimonidine) were significantly higher than the mean IOP at baseline at 8:00 am. Higher IOP was also observed at days 7, 14, 56, and 89/90 at 4:00 pm for eyes treated with APF 423.

At day 30, mean IOP for eyes treated with APF 255 POE implants (200 µg brimonidine) was significantly lower than the mean IOP at baseline for placebo treated eyes at 8:00 am and noon. At day 56, mean IOP for eyes treated with APF 255 was significantly lower than the mean IOP for base at 8:00 am and noon.

At day 30, mean IOP for eyes treated with APF 260 POE implants (200 µg brimonidine) was significantly lower than the mean IOP for baseline at 8:00 am and lower than the mean IOP for baseline and placebo-treated eyes at noon.

At day 56, the mean IOP at 8:00 am, noon, and 4:00 pm for eyes treated with PLGA1206_01 microspheres (20 μg brimonidine) was significantly lower than the mean IOP for baseline.

Following a single bilateral subconjunctival implantation of APF 255 POE, APF 260 POE or APF 423 POE rod, brimonidine was detected at below the limit of quantitation levels in all ocular tissues at every time point up to day 91 post implant, except for the lens tissue at day 8 with the APF 255 POE implant. Following a single subconjunctival implantation of BF9 waver, brimonidine was detected at BLQ levels in all ocular tissues. Following a single subconjunctival injection of 100 μL microspheres, brimonidine was detected at BLQ levels in all tissues at all time points up to day 91 post implant, except for the iris-ciliary body at day 8 and day 33, and the lens at day 8 and day 33.

Plasma brimonidine concentrations were below the lower limit of quantitation in all samples. The concentrations of brimonidine observed are described in Tables 2-7 below

TABLE 2 brimonidine concentration following subconjunctival injection of 100 μL microspheres containing 20 μg brimonidine

| | Brimonidine Concentration | | | | | |
|---|---|---|---|---|---|---|
| Day | Aqueous Humor (ng/mL) | Iris-ciliary body (ng/g) | Lens (ng/g) | Retina (ng/g) | Vitreous Humor (ng/mL) | Plasma (ng/mL) |
| 8 | NC | 4.36 ± 3.04$^a$ | NC | NC | NC | NC |
| 33 | NC | 18.1 ± 3.0$^a$ | 1.40 ± 0.73$^b$ | NC | NC | 0.040$^c$ (BLQ, 0.079) |
| 57 | NC | NC | NC | NC | NC | NC |
| 91 | NC | NC | NC | NC | NC | NC |

In Table 2, NC = not calculable, $^a$means N = 4 and one sample is BLQ, $^b$means N = 4 and two samples are BLQ, and $^c$means N = 2, and one sample is BLQ.

TABLE 3 brimonidine concentrations following subconjunctival injection of 100 μL microspheres containing 200 μg brimonidine

| | Brimonidine Concentration | | | | | |
|---|---|---|---|---|---|---|
| Day | Aqueous Humor (ng/mL) | Iris-ciliary body (ng/g) | Lens (ng/g) | Retina (ng/g) | Vitreous Humor (ng/mL) | Plasma (ng/mL) |
| 8 | NC | 26.9 ± 10.8 | 10.4 ± 9.7$^a$ | NC | NC | NC |
| 33 | NC | NC | 0.703 ± 0.352$^b$ | NC | NC | NC |
| 57 | NC | NC | NC | NC | NC | NC |
| 91 | NC | NC | NC | NC | NC | NC |

In Table 3, NC = not calculable, $^a$means N = 4 and one sample is BLQ, and $^b$means N = 4 and two samples are BLQ.

TABLE 4 brimonidine concentrations following subconjunctival implantation of APF 255 POE containing 200 μg brimonidine

| | Brimonidine Concentration | | | | | |
|---|---|---|---|---|---|---|
| Day | Aqueous Humor (ng/mL) | Iris-ciliary body (ng/g) | Lens (ng/g) | Retina (ng/g) | Vitreous Humor (ng/mL) | Plasma (ng/mL) |
| 8 | NC | NC | 0.463 ± 0.463$^a$ | NC | NC | NC |
| 33 | NC | NC | NC | NC | NC | NC |
| 57 | NC | NC | NC | NC | NC | NC |
| 91 | NC | NC | NC | NC | NC | NC |

In Table 4, NC = not calculable, and $^a$means N = 4 and two samples are BLQ.

TABLE 5 brimonidine concentrations following subconjunctival
implantation of APF 260 POE containing 200 µg brimonidine Brimonidine Concentration

| Day | Aqueous Humor (ng/mL) | Iris-ciliary body (ng/g) | Lens (ng/g) | Retina (ng/g) | Vitreous Humor (ng/mL) | Plasma (ng/mL |
|---|---|---|---|---|---|---|
| 8 | NC | NC | NC | NC | NC | NC |
| 33 | NC | NC | NC | NC | NC | 0.064[a] (BLQ, 0.127) |
| 57 | NC | NC | NC | NC | NC | NC |
| 91 | NC | NC | NC | NC | NC | 0.59[a] (BLQ, 1.17 |

In Table 5, NC = not calculable, and [a]means N = 2 and one sample is BLQ.

TABLE 6 brimonidine concentrations following subconjunctival
implantation of APF 423 POE implant containing 200 µg brimonidine Brimonidine Concentration

| Day | Aqueous Humor (ng/mL) | Iris-ciliary body (ng/g) | Lens (ng/g) | Retina (ng/g) | Vitreous Humor (ng/mL) | Plasma (ng/mL |
|---|---|---|---|---|---|---|
| 8 | NC | NC | NC | NC | NC | NC |
| 33 | NC | NC | NC | NC | NC | NC |
| 57 | NC | NC | NC | NC | NC | 0.267[a] (0.267, BLQ) |
| 91 | NC | NC | NC | NC | NC | 0.084[a] (BLQ, 0.167) |

In Table 6, NC = not calculable, and [a]means N = 2 and one sample is BLQ.

TABLE 7 brimonidine concentrations following subconjunctival
implantation of a wafer containing 250 µg brimonidine Brimonidine Concentration

| Day | Aqueous Humor (ng/mL) | Iris-ciliary body (ng/g) | Lens (ng/g) | Retina (ng/g) | Vitreous Humor (ng/mL) | Plasma (ng/mL |
|---|---|---|---|---|---|---|
| 8 | NC | NC | NC | NC | NC | NC |
| 33 | NC | NC | NC | NC | NC | NC |
| 57 | NC | NC | NC | NC | NC | NC |
| 91 | NC | NC | NC | NC | NC | 0.032[a] (BLQ, 0.063) |

In Table 7, NC = not calculable, and [a]means N = 2 and one sample is BLQ.

In the above, the samples were quantified using LC-MS/MS methods with quantitation limits of 10 ng/mL for aqueous and vitreous humor samples, 0.05 ng/mL for plasma samples, 0.5 ng for iris-ciliary body samples, lens samples, and retina samples.

In summary, subconjunctival administration of polymeric drug delivery systems containing 20-250 µg of brimonidine was unable to deliver sufficient amounts of brimonidine to the aqueous humor to reduce IOP. Using these drug delivery systems and methods of delivery, therapeutic intraocular concentrations of brimonidine were not observed.

Example 4

Manufacture and Testing of Drug Delivery Systems Containing an Anteriorly Cleared Alpha 2 Adrenergic Receptor Agonist and a Biodegradable Polymer Matrix Biodegradable drug delivery systems are made by combining a anteriorly cleared alpha 2 adrenergic receptor agonist with a biodegradable polymer composition in a stainless steel mortar. The combination is mixed via a Turbula shaker set at 96 RPM for 15 minutes. The powder blend is scraped off the wall of the mortar and then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods have dimensions of about 2 mm long×0.72 mm diameter. The rod implants weigh between about 900 pg and 1100 µg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 µg and 1100 µg.

In-vitro release testing can be performed on each lot of implant (rod or wafer). Each implant may be placed into a 24 mL screw cap vial with 10 mL of Phosphate Buffered Saline solution at 37° C. and 1 mL aliquots are removed and replaced with equal volume of fresh medium on day 1, 4, 7,14, 28, and every two weeks thereafter.

Drug assays may be performed by HPLC, which consists of a Waters 2690 Separation Module (or 2696), and a Waters 2996 Photodiode Array Detector. An Ultrasphere, C-18 (2), 5 µm; 4.6×150 mm column heated at 30° C. can be used for separation and the detector can be set at 264 nm. The mobile phase can be (10:90) MeOH—buffered mobile phase with a flow rate of 1 mL/min and a total run time of 12 min per sample. The buffered mobile phase may comprise (68:0.75:0.25:31) 13 mM 1-Heptane Sulfonic Acid, sodium salt—glacial acetic acid—triethylamine—Methanol. The release rates can be determined by calculating the amount of drug being released in a given volume of medium over time in µg/day.

The polymers chosen for the implants can be obtained from Boehringer Ingelheim or Purac America, for example. Examples of polymers include: RG502, RG752, R202H, R203 and R206, and Purac PDLG (50/50). RG502 is (50:50) poly(D,L-lactide-co-glycolide), RG752 is (75:25) poly(D,L-lactide-co-glycolide), R202H is 100% poly(D, L-lactide) with acid end group or terminal acid groups, R203 and R206 are both 100% poly(D, L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700,11200, 6500,14000, 63300, and 9700 daltons, respectively.

Example 5

Treatment of Glaucoma with an Anteriorly Cleared Alpha 2 Adrenergic Receptor Agonist Implant A 58 year old man diagnosed with glaucoma is treated by administration of a biodegradable drug delivery system administered to each eye of the patient. A 1 mg intravitreal implant containing about 500 μg of PLGA and about 500 μg of an anteriorly cleared alpha 2 adrenergic receptor agonist is placed in his left eye at a location that does not interfere with the man's vision. A similar implant is administered subconjunctivally to the patient's right eye. A more rapid reduction in intraocular pressure in the right eye appears to be due to the location of the implant. After about 3 months from the surgery, the man's intraocular pressure remains steady at acceptable levels, and degeneration of the optic nerve appears to be reduced.

Example 6

Treatment of Glaucoma with an Anteriorly Cleared Alpha 2 Adrenergic Receptor Agonist Composition A 62 year old woman with glaucoma is treated with an intravitreal injection of a solution containing about 20 μg of an anteriorly cleared alpha 2 adrenergic receptor agonist. The patient exhibits an acceptable reduction in elevated intraocular pressure and a decrease in nerve degeneration. The patient reports an overall improvement in quality of life.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. An ophthalmically therapeutic material, comprising:
a therapeutic component comprising a therapeutically effective amount of an alpha 2 adrenergic receptor agonist having a structure effective in providing elimination of the agonist from the anterior chamber of an eye to which the agonist is administered.

2. The material of claim 1, further comprising a liquid carrier component associated with the therapeutic component in the form of a composition suitable for administration to a patient by at least one of intravitreal administration and periocular administration.

3. The material of claim 1, wherein the alpha 2 adrenergic receptor agonist is provided in an amount to provide a therapeutic effect selected from the group consisting of neuroprotection, reduction in intraocular pressure, and combinations thereof.

4. The material of claim 1, wherein the alpha 2 adrenergic receptor agonist has a molecular weight greater than the molecular weight of the alpha 2 adrenergic receptor agonist base structure that is eliminated from the posterior segment of an eye of an individual.

5. The material of claim 1, wherein the alpha 2 adrenergic receptor agonist has a structure effective in providing equal elimination rates from the anterior chamber of the eye and the posterior segment of the eye.

6. The material of claim 1, wherein the alpha 2 adrenergic receptor agonist has a structure effective in providing an anterior elimination rate greater than the posterior elimination rate.

7. The material of claim 1, wherein the material is suitable for administration to an eye and delivers the alpha 2 adrenergic receptor agonist to a region of the eye selected from the group consisting of the anterior chamber of the eye, the posterior chamber of the eye, or combinations thereof.

8. The material of claim 1, further comprising an excipient component.

9. The ophthalmically therapeutic material according to claim 1, wherein said alpha 2 adrenergic receptor agonist has a base structure comprising brimonidine.

* * * * *

UNITED STATES PATENT AND TRADEMARK OFFICE
CERTIFICATE OF CORRECTION

PATENT NO. : 7,931,909 B2
APPLICATION NO. : 11/416929
DATED : April 26, 2011
INVENTOR(S) : Patrick M. Hughes et al.

It is certified that error appears in the above-identified patent and that said Letters Patent is hereby corrected as shown below:

On Title page, field (56), under "OTHER PUBLICATIONS", in column 2, line 8, delete "fluoroscein" and insert -- fluorescein --, therefor.

In column 1, line 10, delete "2004," and insert -- 2005, --, therefor.

In column 1, line 13, delete "administered;" and insert -- administered, --, therefor.

In column 1, line 39, delete "has," and insert -- has --, therefor.

In column 2, line 39, delete "oclludentae" and insert -- occludentae --, therefor.

In column 2, line 43-44, delete "chloramphenical" and insert -- chloramphenicol --, therefor.

In column 5, line 51, delete "acute-macular" and insert -- acute macular --, therefor.

In column 5, line 60, delete "opthalmia;" and insert -- ophthalmia; --, therefor.

In column 6, line 67, delete "receptor-agonist" and insert -- receptor agonist --, therefor.

In column 7, line 5, delete "iris-cilary" and insert -- iris-ciliary --, therefor.

In column 8, line 7, delete "dissociates," and insert -- dissociates --, therefor.

In column 11, line 50, delete "fluoroscein" and insert -- fluorescein --, therefor.

In column 13, line 27, delete "receptortagonist" and insert -- receptor agonist --, therefor.

In column 15, line 42, delete "manitol," and insert -- mannitol, --, therefor.

In column 16, line 27-28, delete "lyophylization" and insert -- lyophilization --, therefor.

In column 16, line 39, delete "asceptic" and insert -- aseptic --, therefor.

In column 16, line 67, delete "measurerment." and insert -- measurement. --, therefor.

In column 24, line 17, delete "ihhibitiors" and insert -- inhibitors --, therefor.

In column 24, line 22, delete "diprivefrine," and insert -- dipivefrine, --, therefor.

In column 24, line 29, delete "inhibitiors" and insert -- inhibitors --, therefor.

In column 25, line 43, delete "loradatine," and insert -- loratadine, --, therefor.

Signed and Sealed this
Twelfth Day of July, 2011

David J. Kappos
*Director of the United States Patent and Trademark Office*

CERTIFICATE OF CORRECTION (continued)
U.S. Pat. No. 7,931,909 B2

In column 25, line 47-48, delete "trimprazine" and insert -- trimeprazine --, therefor.

In column 25, line 48, delete "chiorcyclizine," and insert -- chlorcyclizine, --, therefor.

In column 25, line 52, delete "cefutoxime," and insert -- cefuroxime, --, therefor.

In column 25, line 58, delete "aziocillin," and insert -- azlocillin, --, therefor.

In column 26, line 2, delete "flurometholone," and insert -- fluorometholone, --, therefor.

In column 26, line 5, delete "riamcinolone hexacatonide," and insert -- triamcinolone hexacetonide, --, therefor.

In column 26, line 9, delete "duanorubicin," and insert -- daunorubicin, --, therefor.

In column 26, line 16, delete "immunosuppresive" and insert -- immunosuppressive --, therefor.

In column 26, line 20, delete "valciclovir," and insert -- valacyclovir, --, therefor.

In column 26, line 24, delete "cryotpxanthin, astazanthin," and insert -- cryptoxanthin, astaxanthin, --, therefor.

In column 26, line 38, delete "deliver-additional" and insert -- deliver additional --, therefor.

In column 26, line 53, delete "Serpignous" and insert -- Serpiginous --, therefor.

In column 27, line 9-10, delete "Accosiated" and insert -- Associated --, therefor.

In column 29, line 32, delete "micropsheres" and insert -- microspheres --, therefor.

In column 30, line 39, delete "μm" and insert -- pm --, therefor.

In column 30, line 52, delete "toxicocologically" and insert -- toxicologically --, therefor.

In column 34, line 23, delete "pg" and insert -- μg --, therefor.

In column 34, line 33, delete "7,14" and insert -- 7, 14 --, therefor.

In column 34, line 59, delete "11700,11200, 6500,14000," and insert -- 11700, 11200, 6500, 14000, --, therefor.